United States Patent [19]
McGowan et al.

[11] Patent Number: 5,231,190
[45] Date of Patent: Jul. 27, 1993

[54] SQUARYLIUM COMPOUNDS, AND PROCESSES AND INTERMEDIATES FOR THE SYNTHESIS OF THESE COMPOUNDS

[75] Inventors: Donald A. McGowan, Bedford; Paulina P. Garcia, Arlington; John W. Lee, Still River, all of Mass.; Thomas K. Spencer, Lexena, Kans.; Stephen J. Telfer; Michael J. Zuraw, both of Arlington, Mass.

[73] Assignee: Polaroid Corporation, Cambridge, Mass.

[21] Appl. No.: 696,222

[22] Filed: May 6, 1991

[51] Int. Cl.$^5$ .................. C07D 335/00; C07D 335/06; C07D 345/00

[52] U.S. Cl. .......................... 549/13; 549/23; 549/28; 549/398; 549/399; 549/404; 549/416; 549/427; 549/424; 549/418; 549/403; 562/899

[58] Field of Search .................... 549/13, 28, 399, 403, 549/398, 23, 427, 416, 404, 424, 418; 562/899

[56] References Cited

U.S. PATENT DOCUMENTS

| | | | |
|---|---|---|---|
| 3,617,270 | 6/1969 | Kampfer | 96/1.7 |
| 4,175,956 | 11/1979 | Haley et al. | 430/37 |
| 4,343,948 | 8/1982 | Kawamura et al. | 549/13 |
| 4,353,971 | 10/1982 | Chang et al. | 430/58 |
| 4,387,155 | 6/1983 | Hill et al. | 430/217 |
| 4,507,480 | 3/1985 | Horgan et al. | 546/94 |
| 4,508,811 | 4/1985 | Gravesteijn et al. | 430/270 |
| 4,524,219 | 6/1985 | Law | 564/307 |
| 4,585,884 | 4/1986 | Lin et al. | 556/413 |
| 4,585,895 | 4/1986 | Law | 564/307 |
| 4,602,263 | 7/1986 | Borrer et al. | 346/201 |
| 4,606,986 | 8/1986 | Yanus et al. | 430/59 |
| 4,624,904 | 11/1986 | Kazmaier et al. | 430/59 |
| 4,663,518 | 5/1987 | Borrer et al. | 235/487 |
| 4,751,327 | 6/1988 | Kazmaier et al. | 564/307 |
| 4,826,976 | 5/1989 | Borrer et al. | 544/58.4 |
| 4,830,786 | 5/1989 | Pease et al. | 260/396 |
| 4,886,722 | 12/1989 | Law et al. | 430/59 |
| 4,922,018 | 5/1990 | Law et al. | 564/307 |
| 4,927,970 | 5/1990 | Douglas et al. | 564/462 |
| 5,002,812 | 3/1991 | Umehara et al. | 428/64 |
| 5,026,923 | 6/1991 | Kemp | 568/618 |
| 5,028,660 | 7/1991 | Kobashi et al. | 528/148 |
| 5,030,684 | 7/1991 | Rauch-Puntigam et al. | 524/513 |
| 5,030,759 | 7/1991 | Bayer et al. | 564/401 |
| 5,084,592 | 1/1992 | Schrott et al. | 562/501 |

FOREIGN PATENT DOCUMENTS

| | | |
|---|---|---|
| 2011344 | 2/1970 | France . |
| 58-220143 | 12/1983 | Japan . |
| 61-167681 | 7/1986 | Japan . |
| WO88/04237 | 6/1988 | PCT Int'l Appl. . |

OTHER PUBLICATIONS

M. Palmer, "The Structure and Recations of Heterocyclic Compounds" pp. 252-255, Eduard Arnold (Publishers) LTD, London, (1967).
N. Kuramoto et al., Dyes and Pigments, vol. 11, pp. 21-35, (1989).
"Hackh's Chemical Dictionary," 4th ed., J. Grant ed., p. McGraw-Hill Book Co., New York (1969).
Triebs, A., and Jacob, K., Liebigs Ann. Chem., 712, 123 (1968).
Chemical Abstracts 107, 43057u (1987).
Chemical Abstracts 99, 61698z (1983).
Cohen S. and Cohen, S. G., J. Am. Chem. Soc, 88, 1533 (1966).
DeSelms, R. C., Fox, C. J., and Riordan, R. C., Tetrahedron Letters, 1970, 781.
Hori et al., Angew. Chem. Int. Edn. 29(4), 424-425 (1990).
Kazmaier et al., "The Photogenerating Properties of Unsymmetrical Squaraines and Squaraine Composites", J. Imag. Sci., 32, 1-4 (1988).
Muller et al. Liebig's Ann. Chem, (1973), 1583-1591.
Maahs, et al., "Syntheses and Derivatives of Squaric Acid", Angew. Chem. Int. Ed., 5, 888-893 (1966).
Metler, T. et al., Tetrahedron, 24, 4285 (1968).
Nakagawa, K., et al., J. Org. Chem., 27, 1597 (1962).
Organic Syntheses, vol. 60, pp. 34-39.
Schmidt, A. H. Synthesis, 1980, 961-994.

Primary Examiner—Richard L. Raymond
Assistant Examiner—M. W. Russell
Attorney, Agent, or Firm—David J. Cole

[57] ABSTRACT

Squarylium compounds of the formula:

(Abstract continued on next page.)

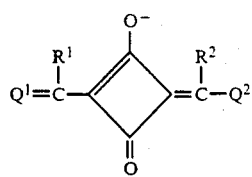

(I)

wherein $Q^1$ and $Q^2$ are each independently a pyrylium, thiopyrylium, selenopyrylium, benzpyrylium, benzthiopyrylium or benzselenopyrylium nucleus, and $R^1$ and $R^2$ are each independently an aliphatic or cycloaliphatic group, can be prepared by reacting a squaric acid derivative of the formula:

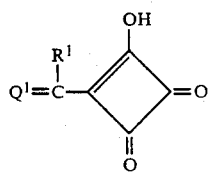

(II)

with a compound of the formula $Q^2CH_2R^2$ in the presence of a base. The derivatives of Formula II may be prepared by condensing a 2,3,4,4-tetrahalocyclobut-2-en-1-one with a compound of the formula $Q^1CH_2R^1$ in the presence of a base to produce a compound of the formula:

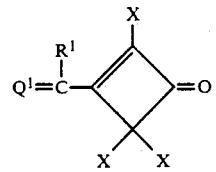

(III)

wherein $Q^1$ and $R^1$ are as defined above, and X represents chlorine or bromine, and hydrolyzing the compound of Formula III. Alternatively, the derivatives of Formula II may be prepared by reacting a diester, monoacid chloride monoester or diacid chloride of squaric acid with a compound of the formula $Q^1CH_2R^1$ in the presence of a base, followed by hydrolysis of the resultant monoacid chloride or monoester derivative of the compound of Formula II to the parent compound.

17 Claims, 3 Drawing Sheets

SQUARYLIUM COMPOUNDS, AND PROCESSES AND INTERMEDIATES FOR THE SYNTHESIS OF THESE COMPOUNDS

BACKGROUND OF THE INVENTION

This invention relates to squarylium compounds, and processes and intermediates for the synthesis of these compounds. More specifically, this invention relates to processes and intermediates useful for the synthesis of squarate dyes (and to such dyes themselves) in which two heterocyclic nuclei are linked to the 1 and 3-positions of a squarate ring via a single, meso $sp^2$ hybridized carbon atom; these dyes will hereinafter be referred to as "pentamethine squarate dyes". The processes of the present invention are especially useful for the synthesis of asymmetric pentamethine squarate dyes, that is to say those in which the two heterocyclic nuclei are dissimilar.

It is known that compounds in which two heterocyclic nuclei are linked by a pentamethine chain, the three central carbon atoms of which form part of a squarate ring, are useful as dyes, especially near infra-red dyes. (The term "near infra-red" is used herein to mean electromagnetic radiation having a wavelength of about 700 to about 1200 nm.) For example, Japanese Patent Application No. 103,604/82 (Publication No. 220,143/83, published Dec. 21, 1983), discloses a broad class of bis-heterocyclic pentamethine dyes in which the central three carbon atoms of the pentamethine chain form part of a squarylium or croconylium ring. The heterocyclic nuclei can be pyrylium, thiopyrylium, selenopyrylium, benzpyrylium, benzthiopyrylium, benzselenopyrylium, naphthopyrylium, naphthothiopyrylium or naphthoselenopyrylium nuclei, which can be substituted with alkyl, alkoxy, aryl or styryl groups.

Japanese Patent Application No. 60-8730 (Publication No. 167,681/86, published Jul. 29, 1986), discloses bis(4-benz[b]thiopyrylium pentamethine dyes in which the central three carbon atoms of the pentamethine chain form part of a squarylium ring. The dyes are intended for use as infra-red absorbers.

U.S. Pat. No. 4,508,811, issued Apr. 2, 1985, describes an optical recording element in which the recording layer comprises a bis(2,6-dialkyl)pyrylium or -thiopyrylium squarylium salt.

Application Ser. No. 07/6;6,639, filed Nov. 21, 1990 by Stephen J. Telfer et al. and assigned to the same assignee as the present application describes 4-[[3-[(benz[b]-4H-pyran-4-ylidene)methyl]-2-hydroxy-4-oxo-2-cyclobuten-I-ylidene]methyl]benz[b]pyrylium hydroxide inner salt dyes, wherein at least one of the benzpyrylium nuclei carries at its 2-position a substituent in which a non-aromatic carbon atom is bonded directly to the benzpyrylium nucleus, subject to the proviso that if this 2-substituent contains an aromatic nucleus, this aromatic nucleus is not conjugated with the benzpyrylium nucleus. These dyes have high absorptions in the near infra-red, and improved solubility in semi-polar solvents and plastics.

Most of these aforementioned pentamethine squarate dyes are symmetrical, that is to say the two heterocyclic nuclei are the same. Such symmetrical dyes are typically prepared by condensing two moles of the appropriate alkyl-substituted heterocyclic compound (in most cases, a salt) with squaric acid in the presence of a base.

In certain applications of pentamethine squarate dyes, it may be advantageous to use a dye which is asymmetric, that is to say a dye which contains two different heterocyclic groupings. For example, some symmetrical near infra-red pentamethine squarate dyes have significant absorption in the visible region, and this visible absorption restricts the utility of the dyes in certain applications, for example thermal imaging media. In particular, if the symmetrical dye absorbs strongly in one part of the visible spectrum but not in another, it will tend to introduce color distortion into any image created using the symmetrical dye. Although asymmetrical analogues of these infra-red pentamethine squarate dyes may have some visible absorption, this visible absorption tends to take the form of a number of separate small peaks, and is thus more spread out over a wide range of wavelengths than in the case of the symmetrical dyes. Such absorption over a range of wavelengths tends to produce lower peak absorption and less color distortion (because the dye tends to produce a grey tint) than that produced by the symmetrical dyes, and thus the asymmetric dyes may advantageously be used in applications where the visible absorption of the symmetric dyes causes problems.

Moreover, there are a number of applications where infra-red dyes are needed which absorb at specific wavelengths. For example U.S. Pat. Nos. 4,602,263 and 4,826,976 both describe thermal imaging systems for optical recording and particularly for forming color images. These patents describe a preferred form of thermal imaging medium for forming multicolor images; in this preferred imaging medium, three separate color-forming layers, capable of forming yellow, cyan and magenta dyes respectively, are superposed on top of one another. Each of the three color-forming layers has an infra-red absorber associated therewith, these absorbers absorbing at differing wavelengths, for example 760, 820 and 880 nm. This medium is imagewise exposed simultaneously to three lasers having wavelengths of 760, 820 and 880 nm. The resultant imagewise heating of the color-forming layers causes the leuco dyes to undergo color changes in the exposed areas, thereby producing a multicolored image, which needs no development. If the choice of infra-red dyes is restricted to symmetrical compounds, it may be difficult to find a dye which absorbs at the precise wavelength required, and which meets the other requirements, such as storage stability and miscibility in polymers, for use in such media. Asymmetric dyes, which allow the two groups linked to the squarylium nucleus to be varied independently, provide an extra degree of freedom which renders it easier to find a dye which absorbs at the desired wavelength and meets the other requirements for use in such media.

However, despite the potential advantages of asymmetric pentamethine squarate dyes, little research has been conducted on such dyes because of the difficulties involved in their synthesis. Although it is possible to modify the conventional alkyl-substituted heterocyclic compound/squaric acid condensation reaction to produce asymmetric pentamethine dyes by including two different heterocyclic compounds in the reaction mixture, such a modified process inevitably produces three different products (two symmetrical dyes and the desired asymmetric dye), thereby wasting at least half the starting materials (and possibly more if one heterocyclic compound is significantly more reactive than the other). Given that the costs of some symmetric pentamethine squarate dyes are high, such materials should be used judiciously and their loss minimized where possible.

Furthermore, separation of the tertiary product mixture produced is difficult, especially since, in many cases of practical importance, the two heterocyclic compounds used are chemically similar. For example, if one attempts to produce the dye of Formula A shown in FIG. 1 in which $R^1$ and $R^2$ are each a hydrogen atom (this dye contains one pyrylium nucleus and one selenopyrylium nucleus) simply by condensing a mixture of the two corresponding salts with squaric acid, it is extremely difficult to separate the desired asymmetric salt from the two even on a laboratory scale and conducting this separation on a commercial scale would be a practical impossibility. In some applications of infrared dyes, the presence of even minor amounts of symmetric by-products in the desired asymmetric dye may cause significant problems. For example in thermal imaging media described in the aforementioned U.S. Pat. Nos. 4,602,263 and 4,826,976, as already noted three separate imaging layers are present having infrared absorbers with absorptions at 760, 820 and 880 nm. Conveniently, two of these three absorbers are Dye A shown in FIG. 1 in which $R^1$ and $R^2$ are each a hydrogen atom and the corresponding bis-selenopyrylium dye. However, if Dye A is contaminated with even a small proportion of the corresponding bis-selenopyrylium dye, serious problems may result in such a medium, in that the bis-selenopyrylium impurity in the layer containing Dye A will absorb the "wrong" radiation, which may lead to unwanted exposure of parts of the layer containing Dye A and a reduction in sensitivity of the medium because the bis-selenopyrylium impurity will absorb a large part of the radiation intended to cause color change in a different color-forming layer.

There is thus a need for a process for the preparation of pentamethine squarate dyes which does not require the separation of mixtures of asymmetric and symmetric products, and which can avoid waste of starting materials.

Processes for the preparation of asymmetric compounds in which two different aromatic nuclei are directly bonded to a squarate ring are known. Kazmaier et al., "The Photogenerating Properties of Unsymmetrical Squaraines and Squaraine Composites", J. Imag. Sci., 32, 1–4 (1988) states that unsymmetrical squaraines can be produced by a two-step route in which the two pendent aromatic groups are attached in separate reactions, and further states that "Unsymmetrical squaraines were synthesized in a multi-step procedure featuring the preparation of 4-(4-dimethylaminophenyl)-3-hydroxycyclobutenedione". However, no further details of this procedure are given.

U.S. Pat. No. 4,751,327 and U.S. Pat. No. 4,624,904 describe unsymmetrical squaraines for use in photoconductive imaging members. Columns 8–10 of each patent describe two synthetic methods for the preparation of these squaraines, these methods involving condensation of a diacid chloride or diester of squaric acid with one mole of a first amine, to form the appropriate 4-aminophenyl squarate derivative, hydrolysis of this derivative to introduce a 2-hydroxyl group on the squarate ring, and a second condensation to introduce at the 3-position of the squarate ring a second and different 4-aminophenyl group.

U.S. Pat. No. 4,922,018 and U.S. Pat. No. 4,886,722 describe unsymmetrical squaraines and their use in photoconductive imaging members. These squaraines are prepared by condensing, for example, a 1-alkoxyaryl-2-hydroxycyclobutene-3,4-dione derivative with an N,N-dialkylaniline derivative in the presence of an aliphatic alcohol and optionally a drying reagent. The squarate derivative is formed by a 2+2 cycloaddition process involving a tetraalkoxyolefin and an alkoxyarylketene generated in situ by the reaction of an alkoxyarylacetyl chloride and a base. The conditions of this cycloaddition reaction limit the substituents which can be present on the alkoxyarylacetyl chloride. Furthermore, the syntheses of the alkoxyarylacetyl chlorides required may be difficult.

The present invention provides processes which can be used to prepare asymmetric pentamethine squarate dyes, and intermediates produced by such processes.

SUMMARY OF THE INVENTION

This invention provides a process for the preparation of a squarylium compound of the formula:

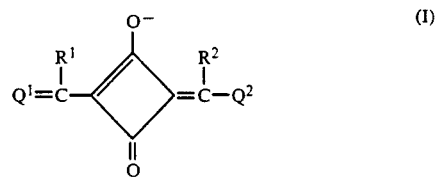
(I)

wherein $Q^1$ and $Q^2$ are each independently a heterocyclic nucleus such that in the compounds of formulae $Q^1CH_2R^1$ and $Q^2CH_2R^2$ the methylene hydrogens are active hydrogens, and $R^1$ and $R^2$ are each independently a hydrogen atom or an aliphatic or cycloaliphatic group. This process comprises reacting a squaric acid derivative of the formula:

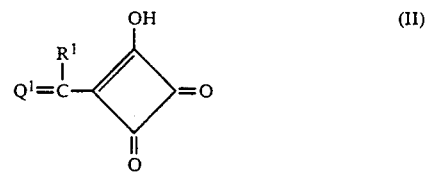
(II)

wherein $Q^1$ and $R^1$ are as defined above, with a compound of the formula $Q^2CH_2R^2$ in the presence of a base. This reaction will hereinafter be referred to as the "dye-forming" reaction of the invention.

This invention also provides a first process for the preparation of a squaric acid derivative of Formula II as defined above, which process comprises hydrolyzing a trihalosquaric acid derivative of the formula:

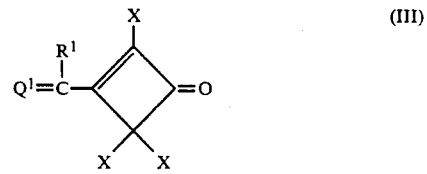
(III)

wherein $Q^1$ and $R^1$ are as defined above, and X represents chlorine or bromine. This process will hereinafter be referred to as the "trihalosquaric hydrolysis" reaction of the invention.

This invention also provides a second process for the preparation of a squaric acid derivative of Formula II as defined above, which process comprises reacting a diester, monoacid chloride monoester or diacid chloride of squaric acid with a compound of the formula $Q^1CH_2R^1$ (wherein $Q^1$ is a heterocyclic nucleus such that in the compound of formula $Q^1CH_2R^1$ methylene hydrogens are active hydrogens, subject to the proviso that in $Q^1$ a carbon atom is bonded to the carbon atom carrying the group $R^1$ is not bonded directly to a nitrogen atom, and $R^1$ is as defined above), followed by hydrolysis of the resultant monoacid chloride or monoester intermediate. This reaction will hereinafter be referred to as the "salt condensation" reaction of the invention.

This invention also provides a process for the preparation of a trihalosquaric acid derivative of the Formula (III) as defined above, which process comprises condensing a 2,3,4,4-tetrahalocyclobut-2-en-1-one with a compound of the formula $Q^1CH_2R^1$ in the presence of a base. This reaction will hereinafter be referred to a the "trihalosquaric formation reaction".

This invention also provides a squaric acid derivative of the formula:

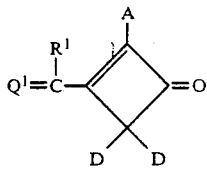

wherein $Q^1$ is a heterocyclic nucleus such that in the compounds of formulae $Q^1CH_2R^1$ and $Q^2CH_2R^2$ the methylene hydrogens are active hydrogens, and $R^1$ is a hydrogen atom or an aliphatic or cycloaliphatic group; and each A and D is a chlorine or bromine atom.

This invention also provides a squaric acid derivative of the formula:

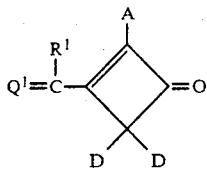

wherein $Q^1$ is a heterocyclic nucleus such that in the compound of formula $Q^1CH_2R^1$ the methylene hydrogens are active hydrogens, subject to the proviso that in $Q^1$ a carbon atom is bonded to the carbon atom carrying the group $R^1$ is not bonded directly to a nitrogen atom, and $R^1$ are as defined above; and A is a chlorine or bromine atom, a hydroxyl group or an esterified hydroxyl group, and the two groups D together form an oxo group.

This invention also provides a squarylium compound of Formula I above wherein $Q^1$ and $Q^2$ are each independently a heterocyclic nucleus such that in the compounds of formulae $Q^1CH_2R^1$ and $Q^2CH_2R^2$ the methylene hydrogens are active hydrogens, the atoms of $Q^1$ and $Q^2$ which are bonded directly to the $CR^1$ and $CR^2$ groupings respectively each being part of an aromatic ring, and $Q^1$ and $Q^2$ are different, and $R^1$ and $R^2$ are each independently a hydrogen atom or an aliphatic or cycloaliphatic group.

It will be noted that the symbol $Q^1$ has been used for both a divalent grouping in Formula I and a monovalent grouping in the formula $Q^1CH_2R^1$. This apparent anomaly is due to the fact that the bond orders in the compounds of Formula I (and indeed in the compounds of Formulae II, III and IV also) are not integral. For example, the dye A shown in the accompanying drawing is actually a resonance hybrid of the form shown and:

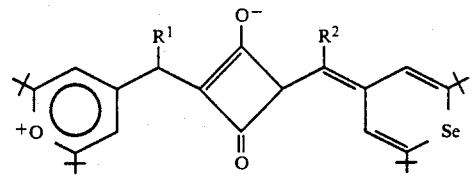

(with contributions from other resonance forms). Thus, whether $Q^1$ is drawn as divalent or monovalent depends solely upon which of the contributing resonance forms is drawn, and similarly for $Q^2$. On the other hand, the compounds of formula $Q^1CH_2R^1$, such as the salt B shown in the drawing, are not resonance hybrids to any significant extent, and thus in this formula $Q^1$ is correctly shown as monovalent. The $Q^1/Q^2$ nomenclature employed will thus be clear to skilled chemists.

The dyes produced by the processes of the present invention may be cationic, anionic or non-ionic. When neither of the nuclei $Q^1$ and $Q^2$ carries any charged substituents, the $Q^1Q^2$-squarate moiety (hereinafter referred to simply as the "dye moiety") is uncharged, and hence the dye is non-ionic. However, if either of the nuclei $Q^1$ and $Q^2$ carries a negatively or positively charged group (for example a $—COO^-$ or trialkylammonium substituent), the dye will be anionic or cationic respectively, and will contain a counterion.

When such a counterion is present, it may be any counterion which is not incompatible with the dye moiety and which thus provides a stable salt. The choice of counterion may be important in ensuring the solubility of the dye in various media, and reducing or preventing aggregation of the dye; minimizing aggregation of the dye is highly desirable since such aggregation can significantly reduce the apparent extinction coefficient of the dye in polymeric media.

Similarly, if the nucleus $Q^1$ or $Q^2$ does not carry any charged substituents (such nuclei being generally preferred in the present processes), the "compounds" $Q^1CH_2R^1$ and $Q^2CH_2R^2$ used in the present processes are actually cations. The counterion present may be any counterion which provides a stable salt and which does not interfere with the relevant reactions. Typically, large fluorinated anions, such as trifluoromethane sulfonate and tetrafluoroborate have been found to give good results in the present processes. The nuclei $Q^1$ and $Q^2$ may, however, bear charged substituents and thus in some cases $Q^1CH_2R^1$ and $Q^2CH_2R^2$ may be neutral compounds which do not require the presence of a counterion.

It may often be found convenient, for synthetic reasons, to prepare a desired moiety with one counterion and thereafter to effect a counterion exchange to form a different salt of the same moiety. Methods for such counterion ion exchange are well known to those skilled in the art.

DETAILED DESCRIPTION OF THE INVENTION

Figure 1:
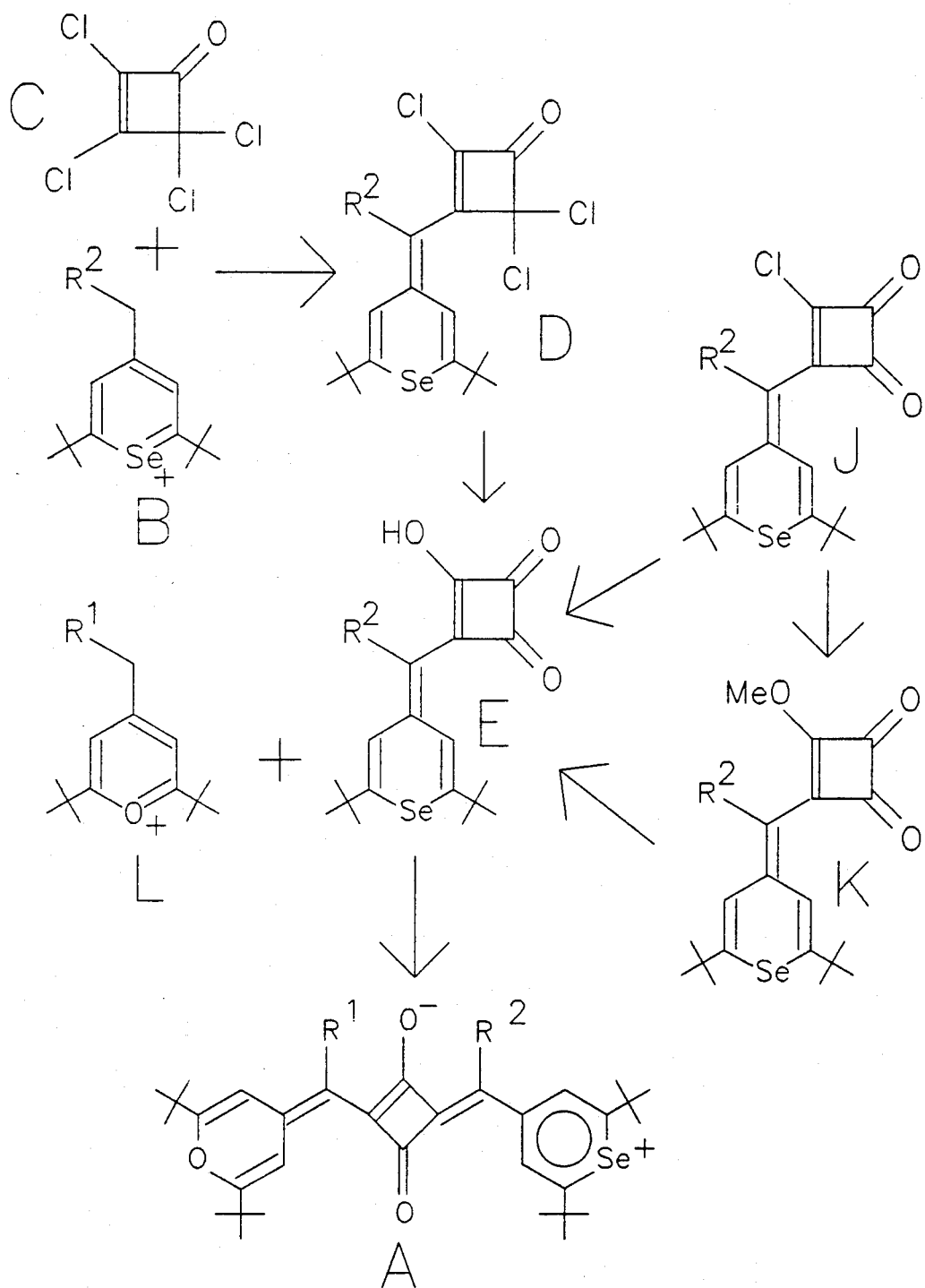
FIGS. 1 and 2 of the accompanying drawings shows a synthetic scheme which may be used to produce an asymmetric pyrylium/selenopyrylium squarate pentamethine dye of the present invention, including some of the reactions described in the Examples below.
Figure 2:
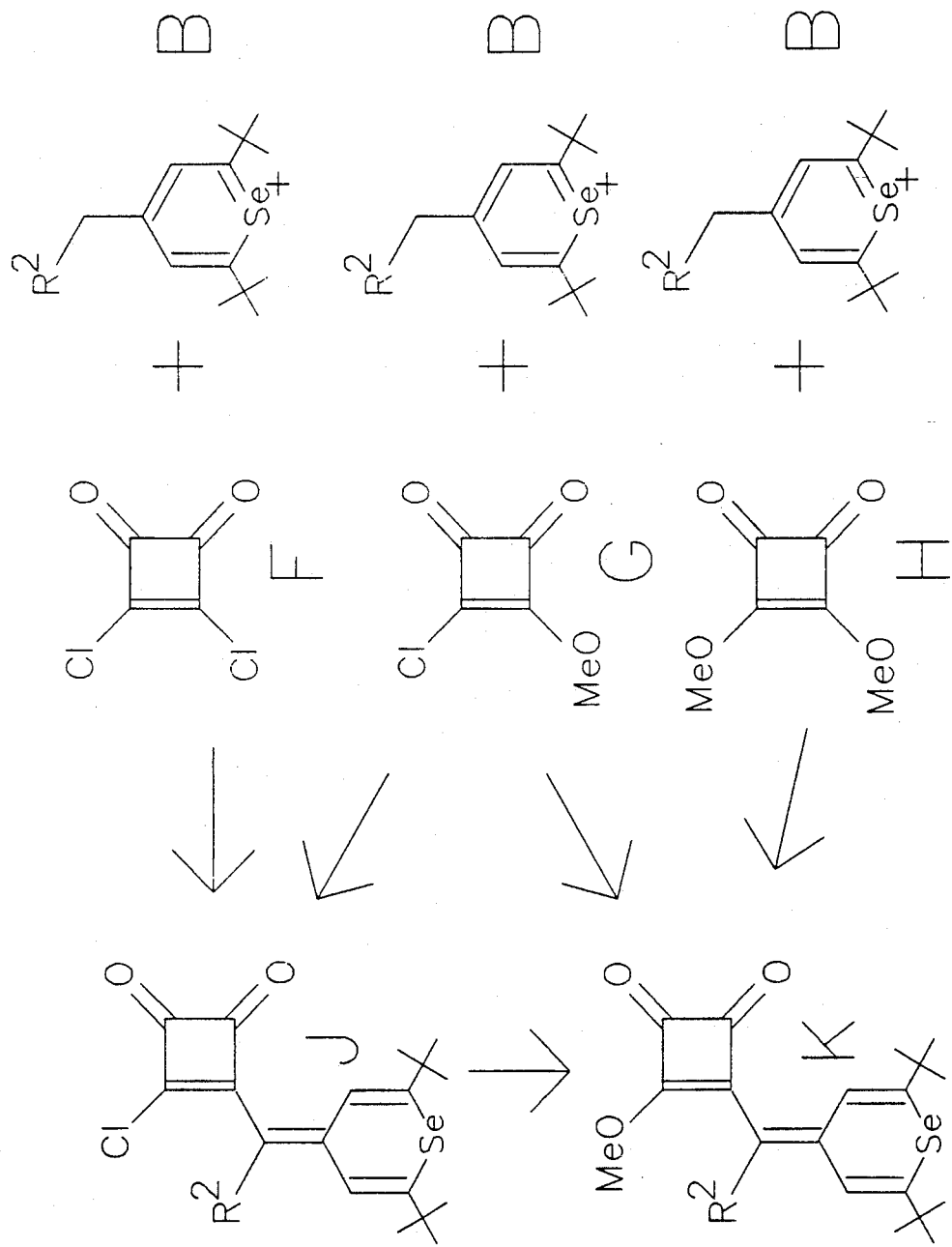
Figure 3:
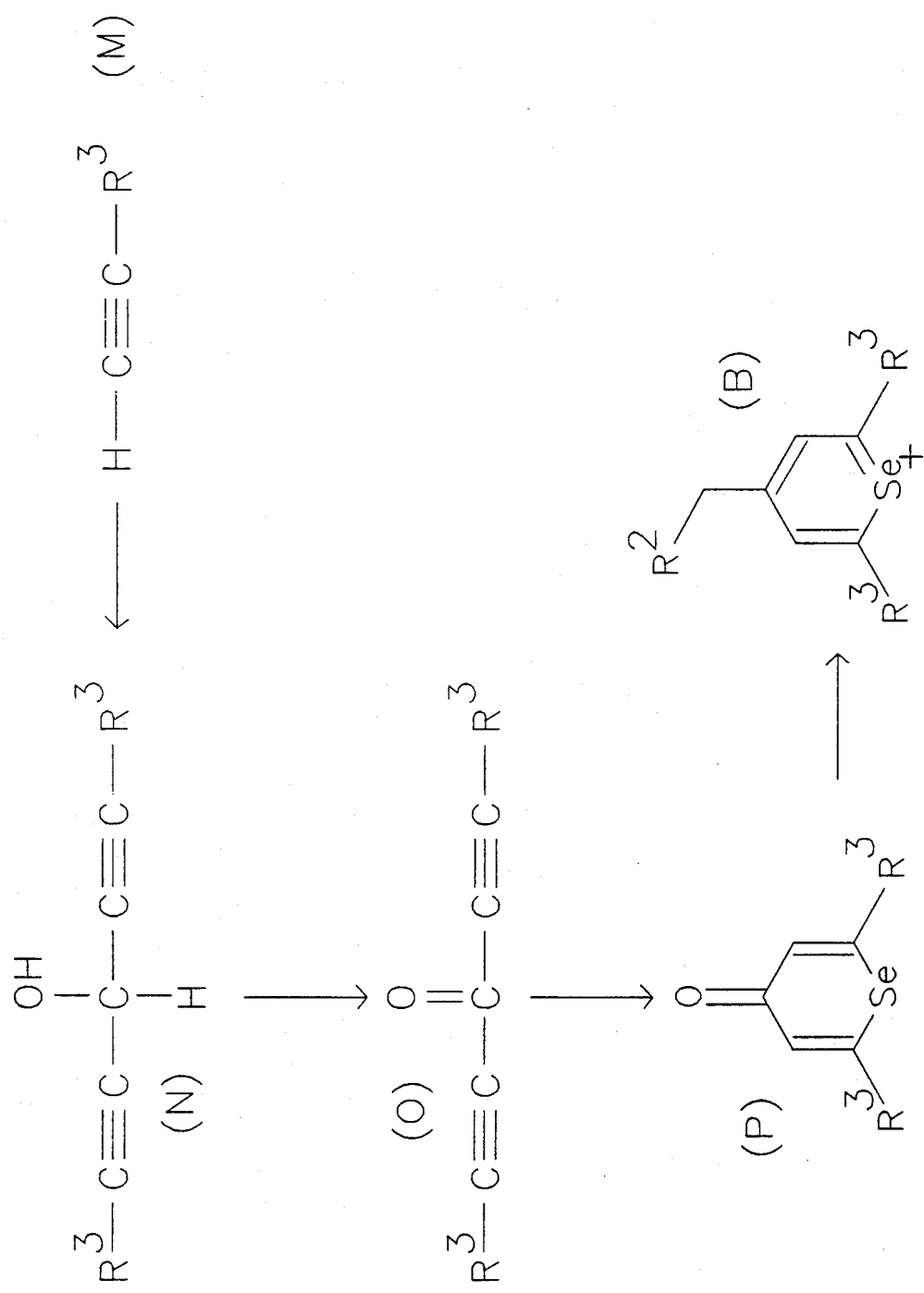
FIG. 3 shows a synthetic scheme used to produce the selenopyrylium salt of Formula B shown in FIGS. 1 and 2.

The interrelationships among the various reactions and intermediates of the present invention may best be seen from, the accompanying drawings, which show in FIGS. 1 and 2 reactions which can be used for the synthesis of a dye A, which is the compound of Formula I in which $R^1$ and $R^2$ are each a hydrogen atom, $Q^1$ is (in the resonance hybrid drawn) a 2,6-bis(1,1-dimethylethyl)pyrylidene group, and $Q^2$ is a 2,6-bis(1,1-dimethylethyl)selenopyrylium group, and in FIG. 3 reactions which can be used to produce the selenopyrylium salt used in the synthesis shown in FIGS. 1 and 2.

As shown in FIG. 1, one form of the synthesis begins with a trihalosquaric formation reaction, the condensation of a 2,6-bis(1,1-dimethylethyl)-4-($R^2$-methyl)-pyrylium salt B (in which $R^2$ is as defined above) with 2,3,4,4-tetrachlorocyclobut-1-en-2-one C to give the trihalosquaric acid derivative D, the compound of Formula IV in which each group A and D is a chlorine atom. The synthesis of the selenopyrylium salt B will be described below with reference to FIG. 3; alternatively, this salt may be prepared by the methods described in Murata et al., Angew. Chem. Int. Edn. 29(4), 424–425 (1990). Methods for the synthesis of the corresponding pyrylium and thiopyrylium salts are described in the literature. The tetrachloro compound C and its synthesis are described in Maahs et al., "Syntheses and Derivatives of Squaric Acid", Angew. Chem. Int. Ed., 5, 888–893 (1966).

This trihalosquaric formation reaction is conducted in the presence, of a base preferably triethylamine. (When the less reactive pyrylium salt is substituted for the selenopyrylium salt B, the reaction is conveniently effected by contacting a solution of the two reactants with a strongly basic resin, for example Baker ANGA-542 (sold by J. T. Baker, 222 Red School Lane, Phillipsburg, N.J. 08865). The solvent used is conveniently an ether, for example tetrahydrofuran. Use of stoichiometric amounts of the two starting materials gives satisfactory results. As noted above, the anion of the salt B can be any anion which provides a stable salt and which does not interfere with the desired reaction; conveniently the tetrafluoroborate salt is used.

As will readily be apparent from FIG. 1, use of the 4-methylselenopyrylium salt B ($R^2$ is a hydrogen atom) will produce a dye in which $R^2$ is hydrogen. If the 4-methyl group of the salt B is replaced with the group of the formula —$CH_2R^2$, the corresponding dyes can be produced in which $R^2$ is an aliphatic or cycloaliphatic group; thus, for example, the use of a 4-ethyl salt gives a final dye in which $R^2$ is methyl. Similar variations in the group $R^1$ are produced by varying the 4-substituent in the pyrylium salt of Formula L (described below). It will be apparent to those skilled in the art that the tetrabromo homologue may be used in place of the tetrachloro compound C.

In the next step of the synthesis, the trihalosquaric hydrolysis reaction, the trihalosquaric acid derivative D is hydrolyzed to the corresponding non-halogenated derivative E. Desirably, this hydrolysis is effected by heating the derivative D with triflic acid, then adding water.

Alternatively, the non-halogenated derivative E may be prepared by the salt condensation reaction of the invention, in which the salt B is condensed with the diacid chloride (F), an ester/acid chloride (G) or a diester (H) of squaric acid, followed by hydrolysis of the resultant product J or K to give the derivative E, as shown in FIG. 1. With both the monoacid chloride/monoester G and the diester H, this reaction requires the presence of a base to produce useful yields. However, with the more reactive diacid chloride F, this reaction can be conducted without base, although in this case the yield is reduced by formation of the compound similar to J but in which the meso carbon atom (that bearing the group $R^2$) bears a proton and the selenopyrylidene ring is replaced by a selenopyrylium ring. The reaction of the diacid chloride F may also be catalyzed by a Lewis acid.

When the diacid chloride F is used as starting material in this reaction, the intermediate is J, the acid chloride of E, whereas when the diester H is used as starting material, the intermediate is K, the ester of E. When the ester/acid chloride G is used, both J and K are produced, but the production of this mixture poses no problems, since both compounds are readily hydrolyzed to give the derivative E. If desired, the acid chloride J may be treated with methanol to convert it to the ester K, and the latter hydrolyzed to give the derivative E. Acid bromides may be used in place of the acid chlorides, and the group $R^2$ may be varied by changing the 4-substituent on the salt B, as described above Also, although the drawings shows use of methyl esters, other ester groups may of course be used.

The acid halides and diesters of squaric acid are known compounds and can readily be prepared by methods known in the art. In addition to the conventional general methods for producing acid halides and esters (for example, reacting squaric acid with 2 equivalents of thionyl chloride in the presence of dimetethylformamide), the aforementioned Maahs et al. paper describes the conversion of 2,3,4,4-tetrachlorocyclobut-2-en-1-one (C) to diesters of squaric acid by reaction with excess alcohol, and the conversion of the same compound C to the diacid chloride F by reaction with oleum or sulfur trioxide with boron trioxide, or antimony pentachloride as catalyst. Although the mixed ester/acid chloride G does not appear to be described in the literature, it is readily prepared by reacting the diacid chloride F with the stoichiometric amount of the appropriate alcohol.

When a base is used to catalyze the salt condensation reaction, this base is conveniently a tertiary amine, for example triethylamine. The intermediates J and K formed by condensation of F, G or H with one mole of the salt B can react with a second mole of this salt to form an unwanted bispyrylium compound. Accordingly, use of excess salt B should be avoided, for example by adding only the stoichiometric amount of the salt.

The conditions needed for the hydrolysis to produce the product E vary somewhat depending upon which of the starting material F, G and H is used. The acid chloride intermediate J can be hydrolyzed simply with water, preferably by heating, whereas the ester intermediate K is preferably hydrolyzed with aqueous mineral acid.

The final step of the synthesis is the dye-forming condensation of the squaric acid derivative E (FIG. 1) with one mole of the appropriate salt $Q^1CH_2R^1$; the salt J in which $Q^1$ is a 2,6-bis(1,1-dimethylethyl)pyrylium group is shown in FIG. 1. As already noted, this salt is described in the literature; the corresponding thiopyrylium salt is described in U.S. Pat. No. 4,343,948, issued Aug. 10, 1982 to Kawamura et al. The conditions required for this reaction are substantially the same as those used for the prior art reactions in which two moles of a pyrylium salt are condensed with squaric acid to form a symmetric bispyrylium dye. Thus, this reaction is assisted by base, conveniently a tertiary amine, for example quinoline. The reaction is desirably conducted in solution in an alcohol, conveniently n-butanol.

Obviously, all the discussion above concerning variations in the 4-substituent and anion of the salt B apply equally to the salt J.

A synthesis of salt B by one of the processes of the present invention is shown in FIG. 3 of the accompanying drawings. Although the salt B shown in FIGS. 1 and 2 is the 2,6-bis(1,1-dimethylethyl) salt, for ease of comprehension FIG. 3 shows the general synthesis of the 2,6-di-$R^3$ salt.

In this synthesis, an $R^3$-acetylene M is reacted with a formate ester in the presence of a base, preferably a Grignard reagent, to give the corresponding 1,5-di-$R^3$-penta-1,4-diyn-3-ol N, which is then oxidized by any of the standard methods for the oxidation of secondary alcohols to ketones, to produce the corresponding 1,5-di-$R^3$-penta-1,4-diyn-3-one O. Condensation of this ketone with selenourea produces the corresponding 2,6-di-$R^3$-selenopyran-4-one P, which is treated with an organometallic alkylating agent, preferably a Grignard reagent to introduce a -$CH_2R^2$ group and the 4-position, thereby yielding the final salt B.

Although the invention has been shown in the accompanying drawings and described above with reference to a compound in which $Q^1$ is a pyrylium nucleus and $Q^2$ is a selenopyrylium nucleus, it will be apparent that both $Q^1$ and $Q^2$ can each independently be any heterocyclic nucleus such that in the compounds of formulae $Q^1CH_2R^1$ and $Q^2CH_2R^2$ the methylene hydrogens are active hydrogens, such that these methylene hydrogen atoms can undergo the condensations with squaric acid derivatives already described. It is preferred that the atoms of $Q^1$ and $Q^2$ which are bonded directly to the $CR^1$ and $CR^2$ groupings respectively each be part of an aromatic ring. For example, $Q^1$ and $Q^2$ may each independently be an imidazole, benzimidazole, thiazole, benzthiazole, oxazole, benzoxazole, 2- or 4-pyridinium, 2- or 4-quinolinium or indolinium nucleus. In the presently preferred process at least one, and desirably both, of $Q^1$ and $Q^2$ is a heterocyclic nucleus in which a carbon atom is bonded directly to the carbon atom carrying the group $R^1$, and this carbon atom is not bonded directly to a nitrogen atom. Desirably, at least one, and desirably both, of $Q^1$ and $Q^2$ is a non-nitrogenous heterocyclic nucleus, especially preferred nuclei being pyrylium, thiopyrylium, selenopyrylium, benzpyrylium, benzthiopyrylium and benzselenopyrylium nuclei. Such nuclei be either the 2- or 4-isomers, although the latter are preferred.

Although the processes of the present invention may be used for the synthesis of both symmetric dyes (when B and L in the drawings are the same) or asymmetric dyes (when B and L are different), they are typically employed to produce asymmetric dyes, since the symmetric dyes can usually readily be prepared by condensing two moles of the appropriate salt with squaric acid. However, there are certain applications (see, for example, the aforementioned U.S. Pat. Nos. 4,602,263 and 4,826,976) which require the use of a plurality of infrared dyes with absorptions at differing wavelengths. To provide an appropriate set of dyes for such an application, it may be convenient to prepare a single intermediate similar to the compound E in the drawing and then to react this single intermediate with a plurality of differing salts to produce the final dyes. In these circumstances, even though one of the final dyes may be symmetric, it may be convenient to produce this symmetric dye by the same route as the asymmetric dyes.

In the squaric acid derivatives of Formula IV, the preferred groups $Q^1$ are as already discussed above with reference to the salt-forming reaction of the invention. In a particularly preferred group of derivatives of Formula IV, $Q^1$ is a 2,6-dialkylpyrylium, -thiopyrylium or -selenopyrylium nucleus, in which each of the alkyl groups contains not more than about 8 carbon atoms, especially those in which $Q^1$ is a 2,6-di-tertiary butyl-pyrylium, -thiopyrylium or -selenopyrylium nucleus. The presence of these nuclei in the final infra-red dyes has been found to provide good solubility in polymeric media and high extinction coefficients. Of these derivatives, those in which the two groups D together form an oxo group, A is a chlorine atom, hydroxyl group or an ester grouping formed from such a hydroxyl group with an alkanol containing not more than about 6 carbon atoms, and $R^1$ is a hydrogen atom or an alkyl group containing not more than about 6 carbon atoms, are preferred. Especially preferred are such derivatives in which A is a hydroxyl group and $R^1$ is a hydrogen atom, namely:

1-[2,6-bis(1,1-dimethylethyl)-4H-pyran-4-ylidene)methyl]-2-hydroxycyclobut-1-en-3,4-dione;
1-[2,6-bis(1,1-dimethylethyl)-4H-thiopyran-4-ylidene)-methyl]-2-hydroxycyclobut-1-en-3,4-dione; and
1-[2,6-bis(1,1-dimethylethyl)-4H-selenopyran-4-ylidene)methyl]-2-hydroxycyclobut-1-en-3,4-dione.

Another preferred group of squaric acid derivatives of Formula IV are those in which $Q^1$ is a 4-benzpyrylium nucleus, desirably such a nucleus which carries at its 2-position a substituent in which a non-aromatic carbon atom is bonded directly to the benzpyrylium nucleus, subject to the proviso that if said 2-substituent contains an aromatic nucleus, this aromatic nucleus is not conjugated with the benzpyrylium nucleus. Preferred 2-substituents are substituted or unsubstituted alkyl or cycloalkyl groups in which the carbon atom which is directly attached to the benzpyrylium nucleus carries not more than one hydrogen atom. Desirably, the benzpyrylium nucleus also carries at its 7-position a substituent in which an element of Group 5A, 6A or 7A of the Periodic Table is directly connected to the benzpyrylium nucleus, subject to the proviso that when this element of Group 5A, 6A or 7A is at least divalent, the 7-substituent may comprise at least one saturated heterocyclic ring containing said element of Group 5A, 6A or 7A, this saturated heterocyclic ring optionally being fused to the phenyl ring of the associated benzpyrylium nucleus; especially preferred 7-substituents are disubstituted amino groups. As described in copending Application Ser. No. 07/616,639 filed Nov. 21, 1990, symmetrical pentamethine squarate dyes containing such 4-benzpyrylium nuclei have desirable properties, including solubility in polymeric media and high extinction coefficients, and asymmetric dyes containing such benzpyrylium nuclei tend to display the same desirable properties.

The dyes produced by the processes of the present invention may be used in any of the applications in which prior art near infra-red absorbers have been used. Thus, the dyes may be used as dyes in printing inks intended to provide markings which can be read under near infra-red radiation, for example, on packages of consumer items intended to be scanned by near infra-red laser scanners. At least some of the present dyes may also be useful as charge transfer materials for use in xerography, electrophotography and similar processes, and as laser dyes.

However, because of their high extinction coefficients in the near infra-red region, the dyes produced by the present processes are especially useful in processes for generating heat in a medium; in such a process at least part of the medium is exposed to near infra-red actinic radiation of a frequency absorbed by the dye, so that the radiation is absorbed by the dye and heat is generated within the parts of the medium exposed to the radiation. Typically, in such a process, the radiation is provided by a laser. The medium may also comprise a thermally sensitive material capable of undergoing a color change upon exposure to heat; the medium is exposed imagewise to the radiation, and the heat generated by the dye is sufficient to effect a color change in the thermally sensitive material, so that an image is formed in the medium. Thus, for example, the present dyes may be used as the near infra-red absorbers in the thermal imaging processes described in the aforementioned U.S. Pat. Nos. 4,602,263 and 4,826,976, which rely upon the irreversible unimolecular fragmentation of one or more thermally unstable carbamate moieties of an organic compound to effect a visually discernible color shift from colorless to colored, from colored to colorless or from one color to another.

In such a process, preferably the thermally sensitive material is originally substantially colorless and is converted by the heat generated to a colored material in exposed areas of the image. Multi-colored images may be produced using a heat-sensitive element containing an imaging layer of colorless imaging compound (leuco dye) for forming a yellow image, an imaging layer of colorless imaging compound for forming a cyan image, and an imaging layer of colorless imaging compound for forming a magenta image. Preferred leuco dyes, and processes for their preparation, are described in U.S. Pat. No. 4,663,518, and other preferred yellow-forming leuco dyes are described in Application Ser. No. 07/548,223, filed Jun. 29, 1990.

In the production of such multi-color images, each imaging layer contains, in addition to the leuco dye, an infra-red absorber selected such that the three infra-red absorbers absorb radiation at different predetermined wavelengths above 700 nm sufficiently separated so that each imaging layer may be exposed separately and independently of the others by using infra-red radiation at the particular wavelengths selectively absorbed by the respective infra-red absorbers. As an illustration, the yellow, magenta and cyan precursors may have infra-red absorbers associated therewith that absorb radiation at (say) 760 nm, 820 nm and 880 nm, respectively, and may be addressed by laser sources, for example, infra-red laser diodes emitting radiation at these respective wavelengths so that the three imaging layers can be exposed independently of one another. While each layer may be exposed in a separate scan, it is usually preferred to expose all of the imaging layers simultaneously in a single scan using multiple laser sources of the appropriate wavelengths. Instead of using superimposed imaging layers, the heat-sensitive compounds and associated infra-red absorbers may be arranged in an array of side-by-side dots or stripes in a single recording layer.

Alternatively, the present dyes may be used in a thermal imaging process in which the medium comprises one layer of a multi-layer structure, this structure further comprising a support layer disposed on one side of the medium and a colored layer adhering to the opposed side of the medium. In this type of thermal imaging process, the heat generated on exposure of the dye to actinic radiation causes increased adhesion of the colored layer to the support layer, such that upon application of a peeling force to the colored layer, the colored layer will peel from the support layer in areas which have not been exposed to the radiation, but in areas which have been exposed to radiation the colored layer will remain attached to the support layer. A preferred thermal imaging process of this type is described and claimed in International Patent Application No. PCT/US87/03249.

From the foregoing description, it will be seen that the present invention provides processes and intermediates which enable a wide variety of asymmetric infra-red dyes to be synthesized without the need to separate mixtures of asymmetric and symmetric dyes. Because the present dye-forming reaction does not produce the compounds of Formula I admixed with the corresponding symmetric compounds, the present dye-forming reaction is readily capable of producing compounds of Formula I which are essentially free from squarylium compounds of the formulae:

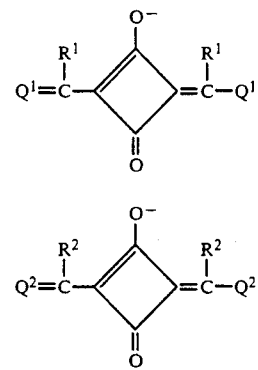

Using the processes of the present invention, syntheses of asymmetric dyes can be carried out in a small number of steps from readily available starting materials and in good yields.

The following Examples are now given, though by way of illustration only, to show details of particularly preferred reagents, conditions and techniques used in the processes of the present invention.

EXAMPLE 1

Preparation of 3-[2,6-di(1,1-dimethylethyl)-(4H-pyran-4-ylidene)methyl]-2,4,4-trichlorocyclobut-2-en-1-one This Example illustrates the preparation by a reaction analogous to B+C→D shown in FIG. 1, of the trichlorosquaric acid derivative of Formula IV in which $Q^1$ is a 2,6-bis(1,1-dimethylethyl)-4-pyrylidene grouping, $R^1$ is a hydrogen atom, and each group A and D is a chlorine atom.

2,6-bis(1,1-dimethylethyl)-4-methylpyrylium trifluoromethane sulfonate (8.0 g, 22.4 mmole, prepared as described in Organic Syntheses, 60, 34-39) and dried Baker ANGA-542 basic resin (40 g, 59.2 meq) were stirred in tetrahydrofuran (300 mL), then 2,3,4,4-tetrachlorocyclobut-2-en-1-one (4.6 g, 3.1 mL, 22.4 mmole, prepared as described in R. C. DeSelms, C. J. Fox, R. C. Riordan, Tetrahedron Letters, 1970, 781; this paper also describes a preparation of the diacid chloride F shown in FIG. 2) was added all at once. The resultant reaction mixture was stirred for a further 4 hours; the color, which had been green after the addition of the tetrachloro compound, gradually changed to orange-brown. The reaction mixture was then filtered, the solvent removed until the residue was almost dry, and the residue recrystallized from boiling toluene to give the trichlorosquaric acid derivative as a yellow, crystalline solid, which gave only a single spot upon thin layer chromatography on silica gel with dichloromethane as eluent. The structure of the product was confirmed by fast atom bombardment (FAB) mass spectroscopy and by proton nuclear magnetic resonance (NMR) spectroscopy. The infra-red spectrum of the product showed bands at 2950, 1770, 1650, 1540 (broad), 1310, 1250, 1200, 940 and 800 cm$^{-1}$.

EXAMPLE 2

Preparation of
3-[2,6-bis(1,1-dimethylethyl)-(4H-pyran-4-ylidene)methyl]-4-hydroxycyclobut-3-ene-1,2-dione This Example illustrates the preparation, by a reaction analogous to D→E shown in FIG. 1, of the acid derivative of Formula IV in which $Q^1$ is a 2,6-bis(1,1-dimethylethyl)-4-pyrylidene grouping, $R^1$ is a hydrogen atom, A is a hydroxyl group and the two groups D together form an oxo group.

3-[2,6-bis(1,1-dimethylethyl)-(4H-pyran-4-ylidene)-methyl]-2,4,4-trichlorocyclobut-2-en-1-one (100 mg, 0.27 mmole, prepared in Example 1 above), was dissolved in triflic acid (1 mL) and the resultant solution heated at 60° C. for 1 hour, 80° C. for a further 2 hours, and finally at 105° C. for 5 hours. The hot mixture was then poured over ice, and the resultant mixture stirred to give a solid precipitate. The mixture was extracted several times with dichloromethane, and the extracts were combined, washed with brine, dried over sodium sulfate and evaporated to dryness. The residue was redissolved in dichloromethane and applied to two preparative silica gel chromatography plates. Elution with 8% methanol in dichloromethane resulted in the development of many minor bands, with a major yellow band streaking from the origin. The major yellow band was extracted with methanol, the resultant solution evaporated to dryness, the residue dissolved in dichloromethane, and the solution filtered and evaporated to dryness. Pumping under high vacuum gave a yellow-brown solid (70 mg, 87% yield). The structure of the product was confirmed by proton NMR spectroscopy.

EXAMPLE 3

Preparation of
4-[[3-2.6-bis(1,1-dimethylethyl)-(4H-pyran-4ylidene)-methyl]-2-hydroxy-4-oxo-2-cyclobuten-1-ylidene]methyl]-2,6-bis(1,1-dimethylethyl)thiopyrylium hydroxide inner salt dye This Example illustrates the preparation, by a reaction analogous to E+L→A shown in FIG. 1, of the squarate dye of Formula I in which $Q^1$ is a 2,6-bis(1,1-dimethylethyl)-4-pyrylidene grouping, $Q^2$ is a 2,6-bis(1,1-dimethylethyl)-4-thiopyrylium grouping, and $R^1$ and $R^2$ are each a hydrogen atom.

3-[2,6-bis(1,1-dimethylethyl)-(4H-pyran-4-ylidene)-methyl]-4-hydroxycyclobut-3-ene-1,2-dione (60 mg, 0.2 mmole, prepared in Example 2 above) and 2,6-bis(1,1-dimethylethyl)-4-methylthiopyrylium tetrafluoroborate (62 mg, 0.2 mmole, prepared as described in U.S. Pat. No. 4,343,948) were mixed with n-butanol (2 mL) and distilled quinoline (23 µL). The resultant mixture was heated at 100° C. for 4 hours, then evaporated to dryness. The residue was partitioned between dichloromethane and water, and the dichloromethane layer separated, washed with water, dried over sodium sulfate and evaporated to dryness. The residue was placed on two preparative silica chromatography plates and eluted with a 1:1 v/v ethyl acetate/dichloromethane mixture. The resulting greenish band was excised, ground in a mortar and extracted with 5% methanol in ethyl acetate. The resultant solution was evaporated to dryness and the residue triturated with dichloromethane. The solution was filtered and evaporated to dryness under high vacuum to give the dye as a greenish metallic crystalline solid (32 mg, 32% yield based on the squarate starting material). The structure of the dye was confirmed by FAB mass spectroscopy and by proton NMR spectroscopy. The dye had a strong infra-red absorption at 768 nm in dichloromethane solution, $\epsilon = 285,000$.

EXAMPLE 4

Preparation of
2.6-bis(1,1-dimethylethyl)-4-methylselenopyrylium tetrafluoroborate This Example illustrates the preparation of the selenopyrylium salt B ($R^3 = 1,1$-dimethylethyl) by the synthetic route shown in FIG. 3, which uses reactions based upon those described in Liebig's Ann. Chem, (1973), 1583; J. Org. Chem., 27, 1597 (1962) and Tetrahedron, 24, 4285 (1968).

Part A: Preparation of
2,2,8,8-tetramethylnona-3,6-diyn-5-ol (N)

3,3-dimethylbut-1-yne (10 g, 122 mmole, available from Aldrich Chemical Company) was dissolved in tetrahydrofuran (150 mL) and the solution was cooled under nitrogen to −60° C. Methyl magnesium chloride (38.0 mL of a 2.9 M solution in tetrahydrofuran, 110 mmole) was added dropwise over a period of 30 minutes, and then the reaction mixture was allowed to warm to room temperature and stirred at room temperature for 16 hours. The resultant clear solution was cooled to −30° C., which resulted in the formation of a thick suspension, and ethyl formate (4.5 mL, 56 mmole) was added dropwise; the resulting reaction was strongly exothermic. After the addition of the ethyl formate had been completed, the reaction mixture was stirred at room temperature for 3 hours, then poured into an ammonium chloride solution and extracted with ether. The ether layer was separated, washed with water, dried over sodium sulfate and evaporated to an oil. Since the proton NMR spectrum of the oil indicated that tetrahydrofuran was still present, the oil was pumped under high vacuum to give 8.43 g of a solid, which was recrystallized from pentane to yield a first crop of 5.31 g and a second crop of 2.1 g of 2,2,8,8-tetramethyl-nona-3,6-diyn-5-ol. The structure of this product was confirmed by FAB mass spectroscopy and by proton NMR spectroscopy.

Part B: Preparation of 2,2,8,8-tetramethylnona-3,6-diyn-5-one (O)

The 2,2,8,8-tetramethyl-nona-3,6-diyn-5-ol prepared in Part A (7.0 g, 36 mmole) was dissolved in 150 mL of benzene, cooled to 5°-10° C. and nickel peroxide (18.15 g, 465 mmole) was added over a period of 20 minutes. After the addition had been completed, the reaction mixture was stirred at room temperature for 30 minutes, then filtered, and the nickel peroxide left on the filter was washed well with benzene and then with dichloromethane. The filtrate was evaporated to give a yellow solid, which was recrystallized from benzene to give 2,2,8,8-tetramethyl-nona-3,6-diyn-5-one as pale yellow crystals (4.2 g). The structure of this product was confirmed by FAB mass spectroscopy.

Part C: Preparation of 2.6-bis(1,1-dimethylethyl)-selenopyran-4-one (P)

Selenourea (2 g, 16.2 mmole) was dissolved under nitrogen in dimethylformamide (3 mL) and the solution was stirred on an ice bath as a solution of the 2,2,8,8-tetramethyl-nona-3,6-diyn-5-one prepared in Part B (1.03 g, 5.4 mmole) in acetonitrile (5 mL) was added dropwise over a period of 15 minutes. The ice bath was then removed and the reaction mixture stirred at room temperature for 3 hours (a precipitate formed after 2 hours), and then allowed to stand at room temperature overnight. The mixture was filtered and the filtrate reduced in volume by evaporation, then ether (50 mL) was added, whereupon a white solid precipitated. The resultant mixture was filtered and the ether evaporated from the filtrate. The remaining dimethylformamide solution was treated with ice water (25 mL) to give a gum, which solidified on standing, and which was then extracted with hexane. The water layer remaining was decanted and extracted twice with hexanes. The resultant combined hexane solution was combined with the hexane extract of the gum, and the combined hexane solution was washed well with water, then with brine, dried over sodium sulfate and evaporated to dryness. The residue was chromatographed on silica using dichloromethane as eluent, to give 4-(1,1-dimethylethyl)-2-(2,2-dimethylpropylidene)-2,3-dihydroselenofuran-3-one (952 mg) as the major product. Further elution with ether gave 2,6-bis(1,1-dimethylethyl)selenopyran-4-one (300 mg, 20% yield based on the acetylenic starting material). The structure of this product was confirmed by FAB mass spectroscopy and by proton NMR spectroscopy.

Part D: Preparation of salt (B)

The 2,6-bis(1,1-dimethylethyl)-selenopyran-4-one prepared in Part C (218 mg, 0.80 mmole) was dissolved in tetrahydrofuran (5 mL, dried over lithium aluminum hydride) under nitrogen and cooled to 0° C. as methyl magnesium chloride (415 µL of a 2.9 M solution in tetrahydrofuran, 1.20 mmole) was added dropwise. The mixture was stirred at 0° C. for 15 minutes, and then for a further 1.5 hours as it was allowed to warm to room temperature, poured into saturated ammonium chloride solution, and the resultant mixture extracted several times with ether. The separated ether extracts were combined and evaporated to yield a crude oil containing the 4-hydroxy-4-methyl-4H-selenopyran intermediate. This oil was dissolved in ethanol and several drops of tetrafluoroboric acid were added with swirling. The resultant mixture was warmed briefly, then evaporated to dryness and partitioned between dichloromethane and water. The dichloromethane layer was dried over sodium sulfate and evaporated to dryness. Trituration with ether gave 2,6-bis(1,1-dimethylethyl)-4-methylselenopyrylium tetrafluoroborate (86 mg, 30% yield based on the selenopyranone starting material) as pale green-grey crystals. The structure of this product was confirmed by FAB mass spectroscopy.

EXAMPLE 5

Preparation of 2.6-bis(1,1-dimethylethyl)-4-methylselenopyrylium tetrafluoroborate This Example illustrates an improved preparation of the same salt B as in Example 4 above.

Part A: Preparation of 2,2,8,8-tetramethylnona-3,6-diyn-5-ol (N)

Methyl magnesium chloride (1 L of a 3M solution in tetrahydrofuran, 3 mol) was added dropwise over a period of 45 minutes to a solution of 3,3-dimethylbut-1-yne (250 g, 3.04 mol) in dry tetrahydrofuran (750 mL) at −30° C. under nitrogen. The cold bath was removed and the reaction mixture was stirred at room temperature overnight. The resultant solution was then cooled to −10° C. and ethyl formate (116 g of material of 97% purity, 1.5 mol) was added dropwise over a period of 30 minutes. The solution was allowed to attain room temperature and stirred at room temperature for 4 hours, then poured into a mixture of ice/water (5L) and acetic acid (500 mL). The resultant mixture was extracted with heptanes (200 mL), the organic layer removed, and the aqueous layer extracted with additional heptanes (200 mL). The combined organic layers were washed with cold water, dried over anhydrous magnesium sulfate, filtered and placed in a freezer overnight. The crystals which resulted were collected by filtration, washed with cold petroleum ether and air-dried to yield 2,2,8,8-tetramethylnona-3,6-diyn-5-ol (162 g, 56% yield). By allowing the filtrate to evaporate and stirring the residue with cold petroleum ether (at −20° C.), an additional 5% yield of the alcohol may be recovered. The structure of this compound was confirmed by mass spectroscopy and by $^1$H and $^{13}$C NMR spectroscopy.

Part B: Preparation of 2,2,8,8-tetramethylnona-3.6-diyn-5-one (O)

For this step in the synthesis, Jones' Reagent was prepared by adding concentrated sulfuric acid (598 g) to a solution of sodium dichromate dihydrate (440 g, 14.78 mol) in water (1320 mL) and diluting the resultant solution with water (to a volume of 2200 mL).

The Jones' reagent (2.2 L) was added dropwise to a solution of 2,2,8,8-tetramethylnona-3,6-diyn-5-ol (500 g, 2.6 mol, prepared in Part A above) in acetone (1.5 L), and the rapid, exothermic reaction which followed was monitored by thin layer chromatography for disappearance of starting material. When this had been observed, the two-phase mixture was poured with agitation into ice/water, and the resultant precipitate was filtered and washed with water until a colorless filtrate was obtained. Air drying afforded 2,2,8,8-tetramethylnona-3,6-diyn-5-one (471 g, 94% yield) as pale yellow crystals which melted at 65°–66° C. The structure of this compound was confirmed by mass spectroscopy and by $^1$H and $^{13}$C NMR spectroscopy.

Part C: Preparation of
2,6-bis(1,1-dimethylethyl)selenopyran-4-one (P)

Lithium triethylborohydride (Super Hydride, available from Aldrich Chemical Company, Milwaukee, Wis., 400 mL of a 1M solution in tetrahydrofuran) was added to selenium powder (16 g, 0.2 mol) under nitrogen. The temperature of the mixture was observed to rise to 45° C. The milky white resultant solution was stirred for 1 hour, after which sodium methoxide (173 g of a 25% solution in methanol) was added and the mixture was cooled to 10° C. Meanwhile, sodium methoxide (108 g of a 25% solution in methanol) was added to a solution of 2,2,8,8-tetramethylnona-3,6-diyn-5-one (38 g, 0.2 mol, prepared in Part B above) in tetrahydrofuran (200 mL) at 5° C. The resultant solution was added in a dropwise fashion over a 30 minute period to the selenide solution prepared above, this solution being kept below 10° C. throughout the addition. The resultant yellow-brown mixture was stirred overnight at room temperature, then poured into a crushed ice slurry (2.5 gal.) with rapid agitation, and stirred for an additional 90 minutes. The product was filtered, and the solid residue was washed with cold water and air dried to afford a brown granular material, which was subjected to Soxhlet extraction at reflux with heptanes (150 mL). The resultant brown solution was allowed to cool and stir for 2 hours as crystals began to form. It was then placed in a freezer for 2 days, after which the product was removed by filtration, washed with cold heptane (−30° C.) and air dried to give tan crystals (14.9 g). The filtrate was allowed to evaporate and the brown residue was stirred with cold heptanes (−30° C.). The resulting tan crystals were removed by filtration, washed with cold heptanes and air dried. They were then combined with the first crop to afford 2,6-bis(1,1-dimethylethyl)-selenopyran-4-one (23.5 g, 43.5% yield) which melted at 83°–84° C.

Part D: Preparation of salt (B)

Methyl magnesium chloride (40 mL of a 3 M solution in tetrahydrofuran, 0.12 mol) was added to a solution of 2,6-bis[1,1-dimethylethyl]selenopyran-4-one (22 g, 0.081 mol, prepared in Part C above) in dry tetrahydrofuran (100 mL) which was initially maintained at −20° C. using a cold bath; the addition was effected at such a rate that the temperature in the reaction vessel did not exceed −15° C. The cold bath was removed, and the pale yellow solution was allowed to stir at room temperature for four hours, during which time a thick slurry formed. The mixture was then poured into ice/water (1 L) with rapid agitation, and tetrafluoroboric acid (200 mL of a 48% aqueous solution) was added. Stirring was continued for a further two hours, after which the mixture was extracted with dichloromethane (3×100 mL). The organic layer was dried over magnesium sulfate and concentrated under reduced pressure to give a tan residue, which was triturated with ether. The solid which resulted was collected by filtration, washed with ether and dried to give 2,6-bis(1,1-dimethylethyl)-4-methylselenopyrylium tetrafluoroborate (24.7 g, 85% yield) as an off-white solid which melted at 65°–66° C. The structure of this compound was confirmed by mass spectroscopy and by $^1$H and $^{13}$C NMR spectroscopy.

EXAMPLE 6

Preparation of
3-[2,6-bis(1,1-dimethylethyl)-(4H-selenopyran-4-ylidene)methyl]-2,4,4-trichlorocyclobut-2-en-1-one This Example illustrates the preparation, by the reaction B+C→D shown in FIG. 1, of the trichlorosquaric acid derivative of Formula IV in which $Q^1$ is a 2,6-bis(1,1-dimethylethyl)-4-selenopyrylidene grouping, $R^1$ is a hydrogen atom, and each group A and B is a chlorine atom.

A 500 mL three-necked round-bottom flask was equipped with a magnetic stirrer, a dropping funnel with a pressure-equalizing side arm, a condenser with a dry nitrogen gas inlet tube and an outlet attached to a succession of scrubbers containing 10% aqueous sodium hydroxide and 10% aqueous lead acetate. Into this flask were placed 2,6-bis(1,1-dimethylethyl)-4-methylselenopyrylium tetrafluoroborate (3.0 g, 8.4 mmole, prepared as in Example 4 above, 2,3,4,4-tetrachlorocyclobut-2-en-1-one (1.7 g, 8.4 mmole) and dichloromethane (150 mL). Stirring was begun and a solution of triethylamine (2.3 mL, 16 mmole) in dichloromethane (50 mL) was added dropwise over a period of 1.5 hours under nitrogen. After the addition of the triethylamine had been completed, the reaction mixture was stirred at room temperature for an additional 1.5 hours, then filtered through a sintered glass funnel containing silica gel (40 g). The silica gel was washed several times with small portions of dichloromethane until the washings were pale orange. The filtrate and washings were combined and evaporated to dryness on a rotary evaporator on a water bath kept at approximately 40° C. The residual green mass was triturated with hexane (60 mL) until maroon crystals formed; these crystals were removed by suction filtration and dried in vacuo at approximately 30° C. to yield 3-[2,6-bis(1,1-dimethylethyl)-(4H-selenopyran-4-ylidene)methyl]-2,4,4-trichlorocyclobut-2-en-1-one (2.2 g, 60% yield).

EXAMPLE 7

Preparation of
3-[2,6-bis(1,1-dimethylethyl)-(4H-selenopyran-4-ylidene)methyl]-2,4,4-trichlorocyclobut-2-en-1-one This Example illustrates an improved preparation of the same trichlorosquaric acid derivative of Formula IV as in Example 6 above.

A solution of triethylamine (14.8 g, 147 mmol) in dichloromethane (40 mL) was added dropwise under nitrogen to a solution of 2,6-bis(1,1-dimethylethyl)-4-methylselenopyrylium tetrafluoroborate (26.2 g, 73.4 mmol, prepared in Examples 4 and 5 above) and 2,3,4,4-tetrachlorocyclobut-2-en-1-one (15.2 g, 73.4 mmol) in dichloromethane (60 mL), contained in a flask equipped with a condenser and an outlet connected to a gas-washing bottle containing 10% aqueous sodium hydroxide solution; the addition was effected at a rate such that the temperature of the reaction mixture did not exceed 35° C. After the addition had been completed, the reaction mixture was stirred for one hour, then applied to a column packed with silica gel. Elution with dichloromethane, followed by evaporation of the solvent under reduced pressure, provided the crude product which was further purified by trituration with trifluoroethanol for one hour to give 3-[[2,6-bis(1,1,-dimethylethyl)-4H-selenopyran-4-ylidene]methyl]-2,4,4-trichlorocyclobut-2-en-1-one (23 g, 71% yield) as maroon crystals. The structure of this compound was confirmed by mass spectroscopy and by $^1$H and $^{13}$C NMR spectroscopy.

EXAMPLE 8

Preparation of 3-[2,6-bis(1.1-dimethylethyl)-(4H-selenopyran-4-ylidene)methyl]-4-hydroxycyclobut-3-ene-1,2-dione This Example illustrates the preparation, by the reaction D→E shown in FIG. 1, of the squaric acid derivative of Formula IV in which $Q^1$ is a 2,6-bis(1,1-dimethylethyl)-4-selenopyrylidene grouping, $R^1$ is a hydrogen atom, A is a hydroxyl group and the two groups D together form an oxo group.

3-[[2,6-bis(1,1-dimethylethyl)-4H-selenopyran-4-ylidene]methyl]-2,4,4-trichlorocyclobut-2-en-1-one (23 g, 52.4 mmol, prepared in Examples 6 and 7 above), trifluoromethanesulfonic acid (80 mL) and water (3 mL) were heated at 105° C. for three hours under nitrogen in a vessel fitted with an outlet connected to a gas-washing bottle containing 10% aqueous sodium hydroxide solution. The resultant dark solution was cooled to room temperature and added slowly to an ice/water mixture with rapid agitation. The resultant red solid was collected by filtration, washed with water and air dried, causing its color to change to an iridescent green. The crude product so obtained was purified by trituration with cyclohexane for three hours. The pure 3-[[2,6-bis(1,1-dimethylethyl)-4H-selenopyran-4-ylidene]methyl]-4-hydroxycyclobut-3-ene-1,2-dione was collected by filtration, washed with cyclohexane, and dried to afford a red material (18 g, 94% yield). The structure of this compound was confirmed by mass spectroscopy and by $^1$H and $^{13}$C NMR spectroscopy.

EXAMPLE 9

Preparation of 4-[[3-2,6-bis(1,1-dimethylethyl)-(4H-selenopyran-4-ylidene)methyl]-2-hydroxy-4-oxo-2-cyclobuten-1-ylidene]methyl]-2,6-bis(1,1-dimethylethyl)pyrylium hydroxide inner salt dye This Example illustrates the preparation, by the reaction E+L→A shown in FIG. 1, of the squarate dye of Formula I in which $Q^1$ is a 2,6-bis(1,1-dimethylethyl)-4-pyrylidene grouping, $Q^2$ is a 2,6-bis(1,1-dimethylethyl)-4-selenopyrylium grouping, and $R^1$ and $R^2$ are each a hydrogen atom.

A 100 mL three-necked round-bottom flask was equipped with a magnetic stirrer, a thermometer, a reflux condenser with a dry nitrogen gas inlet tube and an outlet attached to a succession of scrubbers containing 10% aqueous sodium hydroxide and 10% aqueous lead acetate. Into this flask were placed crude 3-[2,6-bis(1,1-dimethylethyl)-(4H-selenopyran-4-ylidene)methyl]-4-hydroxycyclobut-3-ene-1,2-dione (2.13 g, 5.02 mmole, prepared in Example 8 above), 2,6-bis(1,1-dimethylethyl)-4-methylpyrylium trifluoromethanesulfonate (1.79 g, 5.02 mmole, prepared as described in Organic Syntheses, 60, 34–39), redistilled quinoline (0.69 mL, 5.8 mmole) and n-butanol (40 mL). Stirring was begun and the reaction mixture was heated at 100° C. under nitrogen for 1.5 hours; after this time, thin layer chromatography showed the complete disappearance of the dione starting material. The solvent and the quinoline were completely removed by distillation in vacuo, the blue-black residue was suspended in water (150 mL) and the suspension was extracted with two 150 mL aliquots of dichloromethane. The separated dichloromethane extracts were combined, washed with three 150 mL aliquots of water and dried over sodium sulfate. The drying agent was removed by filtration and the filtrate evaporated to dryness in a rotary evaporator on a water bath kept at approximately 40° C. The resultant blue-black solid was dried in vacuo at approximately 30° C. to give the crude product (3.5 g, approximately 100% yield).

This crude product was purified by medium pressure reversed phase chromatography using a column prepared by slurrying Whatman Partisil 40 ODS 3 bulk medium (sold by Whatman International Ltd, Maidstone, Kent, England) in 10% methanol in water. In use, this column was eluted continuously with 10% water in methanol (1.5 L) under a medium pressure of nitrogen.

The 3.5 g of crude dye was dissolved in 10% water in methanol (650 mL) and filtered; a very small quantity of dark particles was collected on the filter paper. The dye solution was chromatographed on the pre-eluted column under a medium pressure of nitrogen, and 125 mL fractions of eluent were collected. Each fraction was tested by thin layer chromatography using silica gel and a 1:1 v/v ethyl acetate/ dichloromethane mixture as eluent. The fractions containing the desired product were combined and reduced to approximately 100 mL in volume using a rotary evaporator on a water bath kept at approximately 40° C. A solution of sodium chloride (5 g) in water (10 mL) was added to the concentrate, and the resultant mixture extracts with three 120 mL aliquots of dichloromethane. The dichloromethane extracts were combined and dried over sodium sulfate. The drying agent was then removed by filtration and washed with dichloromethane until the washings were colorless. The filtrate and washings were combined and reduced to approximately 3 mL in volume using a rotary evaporator on a water bath kept at approximately 40° C. The resultant residue crystallized after 1 hour at room temperature under a slow stream of nitrogen to olive-green crystals, which were dried in vacuo at approximately 30° C. over calcium sulfate overnight, to give the desired dye (0.8 g). An additional 0.31 g of the same product was isolated from earlier fractions by the same procedure used for the main fractions, for a total yield of 1.1 g, 40% based upon the dione starting material. The structure of the dye was confirmed by FAB mass spectroscopy and by proton NMR spectroscopy. The dye had a strong infra-red absorption at 779 nm in dichloromethane solution, $\epsilon = 265,000$.

EXAMPLE 10

Preparation of 4-[[3-2,6-bis(1,1-dimethylethyl)-(4H-selenopyran-4-ylidene)methyl]-2-hydroxy-4-oxo-2-cyclobuten-1-ylidene]methyl]-2,6-bis(1,1-dimethylethyl)pyrylium hydroxide inner salt dye This Example illustrates an improved preparation of the same squarate dye of Formula I as in Example 9 above.

A solution of 3-[[2,6-bis(1,1-dimethylethyl)-4H-selenopyran-4-ylidene]methyl]-4-hydroxycyclobut-3-en-1,2-dione (6.9 g, 18.9 mmol, prepared in Example 8 above), 2,6-bis(1,1-dimethylethyl)-4-methylpyrylium trifluoromethanesulfonate (7.1 g, 19.9 mmol, prepared as described in Organic Syntheses, 60, 34–39) and quinoline (6.7 g, 20.9 mmol) in n-butanol (100 mL) was heated at 105° C. for 90 minutes, then allowed to cool to room temperature. The resultant green solution was poured into an ice-cold 6:4 methanol/water mixture (1 L) with rapid stirring. The solid which resulted was collected by filtration and air-dried, giving the crude dye (7.3 g). Purification was accomplished by trituration with boiling hexanes for 20 minutes. The product was filtered while hot, washed with hexanes and air-dried, yielding the dye as golden crystals (6.5 g, 62% yield). High Pressure Liquid Chromatographic analysis indicated this material to be 99% pure by weight. This material was spectroscopically identical to material prepared in Example 9 above.

EXAMPLE 11

Preparation of
4-[2,6-bis(1,1-dimethylethyl)seleno-4H-pyran-4-ylidene]methyl-3-chlorocyclobut-3-en-1,2-dione This Example illustrates the preparation, by the reaction B+F→J shown in FIG. 2, of the squaric acid derivative of Formula IV in which $Q^1$ is a 2,6-bis(1,1-dimethylethyl)-4-selenopyrylidene grouping, $R^1$ is atom, A is a chlorine atom and the two groups D together form an oxo group.

Triethylamine (0.67 g, 6.6 mmol) was added dropwise to a solution of 2,6-bis(dimethylethyl)selenopyrylium tetrafluoroborate (i.18 g, 3.3 mmol, prepared in Example 4 above) and 3,4-dichlorocyclobut-3-en-1,2-dione (0.50 g, 3.3 mmol, prepared as described in Schmidt, A. H., Synthesis, 1980, 963) in dichloromethane (10 mL) at room temperature over a period of 45 minutes. The reaction mixture was stirred for an additional 7 hours, whereupon the solvent was removed and diethyl ether (50 mL) was added. The ether solution was filtered and the filtrate was washed with additional ether (50 mL). The ether extracts were reserved, and the solid residue was purified by flash chromatography on silica gel with dichloromethane as the eluent. The chromatographed material was combined with the ether extracts and the resultant solution was concentrated to yield the desired squaric acid derivative as an orange solid (0.62 g, 49% yield). The structure of this compound was confirmed by mass spectroscopy and by $^1H$ and $^{13}C$ NMR spectroscopy.

EXAMPLE 12

Preparation of
4-1,2,6-bis(1,1-dimethylethyl)seleno-4H-pyran-4-ylidene]methyl-3-hydroxycyclobut-3-en-1,2-dione This Example illustrates the preparation, by the reaction J→E shown in FIG. 1, of the squaric acid derivative of Formula IV in which $Q^1$ is a 2,6-bis(1,1-dimethylethyl)-4-selenopyrylidene grouping, $R^1$ is a-hydrogen atom, A is a hydroxyl group and the two groups D together form an oxo group.

A solution of 4-[[2,6-bis(1,1-dimethylethyl)selenopyran-4-ylidene]methyl]-3-chloro-cyclobut-3-en-1,2-dione (212 mg, 0.55 mmol, prepared in Example 11 above) in tetrahydrofuran (10 mL) containing water (2 mL) was heated at reflux for 7 hours. After cooling to room temperature, the mixture was concentrated under reduced pressure. The crude product so obtained was triturated with hexanes, collected by vacuum filtration and washed with more hexanes to give the acid (140 mg, 69% yield) as a red powder. The structure of this compound was confirmed by mass spectroscopy and by $^1H$ and $^{13}C$ NMR spectroscopy. This material was identical, by $^1H$ NMR spectroscopy, to material prepared in Example 6 above.

EXAMPLE 13

Preparation of
3-chloro-4-methoxycyclobut-3-en-1,2-dione

This Example illustrates the preparation of the squaric acid monoester monoacid chloride G shown in FIG. 2.

Thionyl chloride (476 mg, 4.0 mmol) was added to a suspension of 3-hydroxy-4-methoxycyclobut-3-ene-1,2-dione (500 mg, 3.9 mmol, prepared as described in Schmidt, A. H., Synthesis, 1980, 963 and Cohen S. and Cohen, S. G., J. Am. Chem. Soc., 88, 1533 (1966)) and dimethylformamide (0.2 mL) in toluene (5 mL) and the mixture was heated at reflux for one hour to produce an orange solution. The solvent was evaporated and the residue was dissolved in dichloromethane, washed with water, dried over magnesium sulfate and concentrated under reduced pressure. The crude product so obtained was purified by preparative thin-layer chromatography on silica gel with dichloromethane as eluent to give the monoester monoacid chloride (41 mg, 7% yield) as a white solid which melted at 47°–48° C. The structure of this compound was confirmed by mass spectroscopy and by $^1H$ and $^{13}C$ NMR spectroscopy.

EXAMPLE 14

Preparation of
3-chloro-4-methoxycyclobut-3-en-1,2-dione

This Example illustrates an alternative preparation of the same squaric acid monoester monoacid chloride G as in Example 13.

Methanol (32 mg, 1.0 mmol) was added to a solution of 3,4-dichlorocyclobut-3-en-1,2-dione (151 mg, 1.0 mmol, prepared as described in Schmidt, A. H., Synthesis, 1980, 963) in dichloromethane (0.5 mL) and the resultant solution was allowed to stand at room temperature for 8 hours. The solvent was then removed and the crude product was purified by filtration through silica gel with dichloromethane as eluent to give the monoester monoacid chloride as a white, crystalline solid (110 mg, 75% yield). This material was identical, by 13C NMR spectroscopy, to the material prepared in Example 13 above.

EXAMPLE 15

Preparation of
4-[2,6-bis(1,1-dimethylethyl)seleno-4H-pyran-4-ylidene]methyl]-3-methoxycyclobut-3-en-1,2-dione This Example illustrates the preparation, by the reaction B+G→K shown in FIG. 2, of the squaric acid derivative of Formula IV in which $Q^1$ is a 2,6-bis(1,1-dimethylethyl)-4-selenopyrylidene grouping, $R^1$ is a hydrogen atom, A is a methoxy group and the two groups D together form an oxo group.

A solution of triethylamine (76 mg, 0.75 mmol) in dichloromethane (2 mL) was added dropwise over 30 minutes to a solution of 3-chloro-4-methoxycyclobut-3-en-1,2-dione (100 mg, 0.68 mmol, prepared in Example 14 above) and 2,6-bis(1,1-dimethylethyl)-4-methylselenopyrylium tetrafluoroborate (244 mg, 0.68 mmol, prepared in Example 4 above) in dichloromethane (5 mL) at room temperature, and the resultant mixture was allowed to stand at room temperature for 1 hour. The solvent was then removed and the residue was extracted with hexanes. The extracts were filtered and concentrated under reduced pressure, and the resultant red oil was dissolved in methanol and allowed to stand at 5° C. for two days. The solvent was then removed and the crude product was purified by preparative thin layer chromatography on silica gel with 4% methanol/dichloromethane as eluent to give the ester as a red oil (50 mg, 19% yield). The structure of this compound was confirmed by mass spectroscopy and by $^1$H and $^{13}$C NMR spectroscopy.

EXAMPLE 16

Preparation of
4-[[2,6-bis(1,1-dimethylethyl)seleno-4H-pyran-4-ylidene]methyl]-3-hydroxycyclobut-3-en-1,2-dione This Example illustrates the preparation, by the reaction K→E shown in FIG. 1, of the squaric acid derivative of Formula IV in which $Q^1$ is a 2,6-bis(1,1-dimethylethyl)-4-selenopyrylidene grouping, $R^1$ is a hydrogen atom, A is a hydroxyl group and the two groups D together form an oxo group.

A solution of 4-[2,6-bis(1,1-dimethylethyl)seleno-4H-pyran-4-ylidene]methyl]-3-methoxy-cyclobut-3-en-1,2-dione (25 mg, 0.066 mmol, prepared in Example 15 above) in tetrahydrofuran (4 mL) containing 1M hydrochloric acid (0.2 mL) was heated at reflux for 6 hours, then cooled to room temperature and stored for 16 hours. The solution was then concentrated under reduced pressure (water being removed by azeotropic distillation with toluene (3×10 mL)) to afford the acid as a purplish solid (21.6 mg, 90% yield). The structure of this compound, which was found to be slightly impure by $^1$H NMR, was determined by $^1$H and $^{13}$C NMR spectroscopy to be the same as that of the material prepared in Example 12 above.

EXAMPLE 17

Preparation of
4-[[7-diethylamino-2-(1,1-dimethylethyl)benz[b]-4H-pyran-4-ylidene]methyl]-3-butoxycyclobut-3-en-1,2-dione This Example illustrates the preparation, by a reaction analogous to B+H→K shown in FIG. 2 of the squaric acid derivative of Formula IV in which $Q^1$ is a 7-diethylamino-2-(1,1-dimethylethyl)benz[b]-4H-pyran-4-ylidene grouping, $R^1$ is a hydrogen atom, A is an n-butoxy group and the two groups B together form an oxo group. The diester (the analogue of H) used is the di-n-butyl ester of squaric acid.

A solution of 7-diethylamino-2-(1,1-dimethylethyl)-4-methylbenzpyrylium tetrafluoroborate (3.57 g, 10 mmol, prepared as described in copending Application Serial No. 07/616,639, filed Nov. 21, 1990) in dichloromethane (20 mL) was added dropwise over two hours to a solution of di-n-butyl squarate (2.5 g, 11 mmol, available from Aldrich Chemical Company, Milwaukee, Wis.) and triethylamine (2.02 g, 20 mmol) in dichloromethane (30 mL) at room temperature. After the addition had been completed, the reaction mixture was heated under reflux for three hours. The solvent was then removed and diethyl ether (50 mL) was added. The ether solution was filtered and the solid residue was washed with more ether (50 mL). The combined ether extracts were concentrated, and the crude product thus obtained was purified by flash chromatography on silica gel with 30% ether/hexanes as eluent to give 4-[[7-diethylamino-2-(1,1-dimethylethyl)benz[b]-4H-pyran-4-ylidene]methyl]-3-butoxy-cyclobut-3-en-1,2-dione as a red solid (1.35 g, 29% yield) which melted at 145°-146° C. The structure of this compound was confirmed by mass spectroscopy and by $^1$H and $^{13}$C NMR spectroscopy.

(The filtrate from the ether extraction was collected, dissolved in dichloromethane, washed sequentially with 1M hydrochloric acid, a saturated solution of sodium hydrogen carbonate and brine, and dried over magnesium sulfate. Removal of solvent yielded 3,4-bis[[7-diethylamino-2-(1,1-dimethylethyl)benz[b]-4H-pyran-4-ylidene]methyl]cyclobut-3-en-1,2-dione as a green solid (1.14 g, 37% yield) which did not melt below 300° C. The structure of this compound was confirmed by mass spectroscopy and by $^1$H and $^{13}$C NMR spectroscopy.)

EXAMPLE 18

Preparation of
4-[[7-diethylamino-2-(1,1-dimethylethyl)benz[b]-4H-pyran-4-ylidene]methyl]-3-hydroxycyclobut-3-en-1,2-dione This Example illustrates the preparation, by a reaction analogous to K→E shown in FIG. 1, of the squaric acid derivative of Formula IV in which $Q^1$ is a 7-diethylamino-2-(1,1-dimethylethyl)benz[b]-4H-pyran-4-ylidene grouping, $R^1$ is a hydrogen atom, A is a hydroxyl group and the two groups D together form an oxo group.

A solution of 4-[[7-diethylamino-2-(1,1-dimethylethyl)benz[b]-4H-pyran-4-ylidene]methyl]-3-butoxy-cyclobut-3-en-1,2-dione (200 mg, 0.47 mmol, prepared in Example 17 above) in tetrahydrofuran (5 mL) containing 1M hydrochloric acid (0.5 mL) was heated at reflux for 6 hours, then cooled to room temperature and allowed to stand for 15 hours. The mixture was then concentrated under reduced pressure, excess water being removed by azeotropic distillation with toluene (2×10 mL). The crude product so obtained was triturated with ether, collected by vacuum filtration and washed with more ether to give the acid (148 mg, 86% yield) as a yellow powder which decomposed at 172°-173° C. The structure of this compound was confirmed by mass spectroscopy and by $^1$H and $^{13}$C NMR spectroscopy.

EXAMPLE 19

Preparation of
2-chloro-3-[3-ethyl-5-fluorobenzothiazol-2-ylidene1-methyl-4,4-dichlorocyclobut-2-en-1-one This Example illustrates the preparation, by a reaction analogous to B+C→D shown in FIG. 2, of the trihalosquaric acid derivative of Formula III in which each X represents a chlorine atom, $R^1$ is a hydrogen atom and $Q^1$ is a 3-ethyl-5-fluorobenzothiazole nucleus.

Triethylamine (65 mg, 0.64 mmol) was added dropwise over a period of 1 minute to a solution of 3-ethyl-5-fluoro-2-methylbenzothiazolium p-toluenesulfonate (235 mg, 0.64 mmol, prepared as described in U.S. Pat. No. 4,387,155) and 2,3,4,4-tetrachlorocyclobut-2-en-1-one (100 mL) in dimethylformamide (2 mL). After standing for two hours at room temperature, the reaction mixture was poured onto ice and extracted with dichloromethane. The organic phase was washed with water, dried and concentrated under reduced pressure. The crude residue was purified by preparative thin layer chromatography on silica gel with dichloromethane as eluent to give the trihalosquaric acid derivative (30 mg, 13% yield). The structure of this compound was confirmed by mass spectroscopy and by $^1$H NMR spectroscopy.

We claim:

1. A squaric acid derivative of the formula:

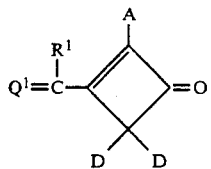

wherein $Q^1$ is a pyrylium, thiopyrylium, selenopyrylium, benzpyrylium, benzthiopyrylium or benzeselenopyrylium nucleus and $R^1$ is a hydrogen atom or an aliphatic or cycloaliphatic group; and each A and D is a chlorine or bromine atom.

2. A squaric acid derivative according to claim 1, wherein $Q^1$ is a 4-pyrylium, 4-thiopyrylium or 4-selenopyrylium nucleus.

3. A squaric acid derivative according to claim 2 wherein $Q^1$ is a 2,6-dialkylpyrylium, -thiopyrylium or -selenopyrylium nucleus, in which each of the alkyl groups contains not more than about 8 carbon atoms.

4. A squaric acid derivative according to claim 3 wherein $Q^1$ is a 2,6-di-tertiary butylpyrylium, -thiopyrylium or -selenopyrylium nucleus.

5. A squaric acid derivative of the formula:

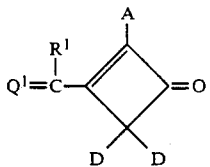

wherein $Q^1$ is a pyrylium, thiopyrylium, selenopyrylium, benzpyrylium, benzthiopyrylium or benzeselenopyrylium nucleus; and $R^1$ is a hydrogen atom or an aliphatic or cycloaliphatic group; and A is a chlorine or bromine atom, a hydroxyl group or an esterified hydroxyl group, and the two groups D together form an oxo group.

6. A squaric acid derivative according to claim 1 wherein $Q^1$ is a 4-pyprylium, 4-thiopyrylium or 4-selenopyrylium nucleus.

7. A squaric acid derivative according to claim 6 wherein $Q^1$ is a 2,6-dialkylpyrylium, -thiopyrylium or -selenopyrylium nucleus, in which each of the alkyl groups contains not more than about 8 carbon atoms.

8. A squaric acid derivative according to claim 7 wherein $Q^1$ is a 2,6-di-tertiary butylpyrylium, -thiopyrylium or -selenopyrylium nucleus.

9. A squaric acid derivative according to claim 8 wherein the two groups D together form an oxo group, A is a chlorine atom, hydroxyl group or an ester grouping formed from such a hydroxyl group with an alkanol containing not more than about 6 carbon atoms, and $R^1$ is a hydrogen atom or an alkyl group containing not more than about 6 carbon atoms.

10. A squaric acid derivative according to claim 9 wherein A is a hydroxyl group and $R^1$ is a hydrogen atom.

11. A squaric acid derivative according to claim 5 wherein $Q^1$ is a 4-benzpyrylium nucleus.

12. A squaric acid derivative according to claim 11 wherein $Q^1$ carries at its 2-position a substituent in which a non-aromatic carbon atom is bonded directly to the benzpyrylium nucleus, subject to the proviso that if said 2-substituent contains an aromatic nucleus, this aromatic nucleus is not conjugated with the benzpyrylium nucleus.

13. A squaric acid derivative according to claim 12 wherein, in $Q^1$, and 2-substituent is a substituted or unsubstituted alkyl or cycloalkyl group, in which the carbon atom which is directly attached to the benzpyrylium nucleus carries not more than one hydrogen atom.

14. A squaric acid derivative according to claim 11 wherein $Q^1$ carries at its 7-position a substituent in which an element of Group 5A, 6A, or 7A of the Periodic Table is directly connected to the benzpyrylium nucleus, subject to the proviso that when said element of Group 5A, 6A or 7A is at least divalent, the 7-substituent may comprise at least one saturated heterocyclic ring containing said element of Group 5A, 6A or 7A, this saturated heterocyclic ring optionally being fused to the phenyl ring of the associated benzpyrylium nucleus.

15. A squaric acid derivative according to claim 14 in which the 7-substituent is a disubstituted amino group.

16. A squaric acid derivative according to claim 5 in solid form.

17. A squaric acid derivative according to claim 5 wherein A is a chlorine or bromine atom, or an esterified hydroxyl group.

* * * * *